United States Patent [19]
Yoon

[11] Patent Number: 5,643,248
[45] Date of Patent: Jul. 1, 1997

[54] MEDICAL INSTRUMENT WITH FORCE LIMITING MECHANISM

[76] Inventor: InBae Yoon, 2101 Highland Ridge Dr., Phoenix, Md. 21131

[21] Appl. No.: 385,182

[22] Filed: Feb. 7, 1995

[51] Int. Cl.$^6$ .................................................. A61B 19/00
[52] U.S. Cl. ........................................................... 606/1
[58] Field of Search .................................. 604/156, 157, 604/95, 158, 162–165, 170, 169, 272, 274, 280, 264; 606/1, 167, 171, 170, 182, 185, 206

[56] References Cited

U.S. PATENT DOCUMENTS

| | | |
|---|---|---|
| 4,535,773 | 8/1985 | Yoon . |
| 5,116,353 | 5/1992 | Green . |
| 5,152,754 | 10/1992 | Plyley et al. . |
| 5,158,552 | 10/1992 | Borgia et al. . |
| 5,215,552 | 6/1993 | Deniega et al. . |
| 5,226,426 | 7/1993 | Yoon . |
| 5,290,243 | 3/1994 | Chodorow ............................ 606/185 |
| 5,290,304 | 3/1994 | Storace . |
| 5,295,993 | 3/1994 | Green . |
| 5,312,354 | 5/1994 | Allen et al. . |
| 5,318,580 | 6/1994 | Gresl ..................................... 606/185 |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,342,382 | 8/1994 | Brinkerhoff et al. . |
| 5,346,459 | 9/1994 | Allen . |
| 5,350,393 | 9/1994 | Yoon . |
| 5,360,405 | 11/1994 | Yoon . |
| 5,372,588 | 12/1994 | Farley et al. . |
| 5,376,082 | 12/1994 | Phelps . |
| 5,397,333 | 3/1995 | Knoepfler ............................ 606/167 |
| 5,462,532 | 10/1995 | Gresl ..................................... 606/185 |

OTHER PUBLICATIONS

Manufacturer's Brochure for "Dial Push–Pull Gauge Model DPP" by Chatillon (one page).

*Primary Examiner*—Glenn Dawson

[57] ABSTRACT

A medical instrument includes a handle, an elongate probe having a proximal end mounted by the handle and a distal end for applying a force to anatomical tissue, and a force limiting mechanism for moving the probe relative to the handle in a direction opposite the applied force when the applied force exceeds a predetermined threshold.

35 Claims, 3 Drawing Sheets

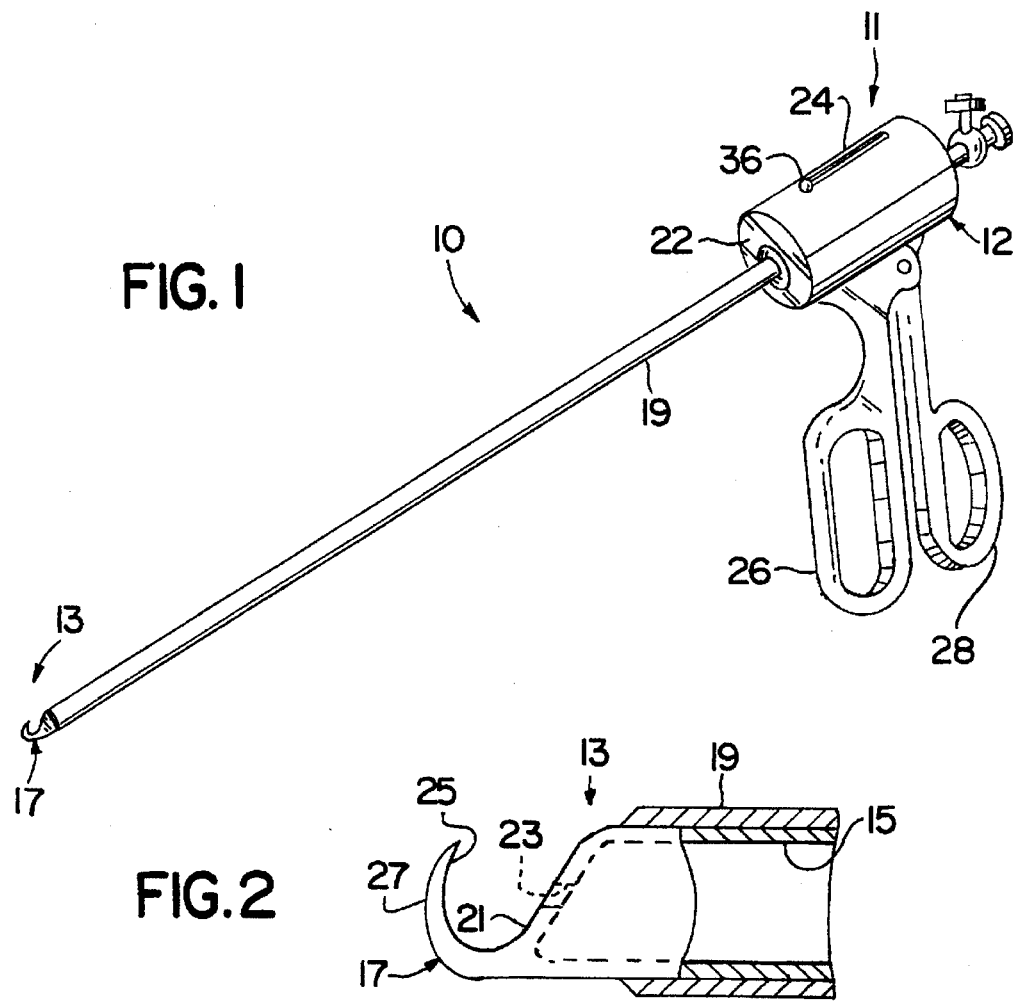
FIG. 1
FIG. 2
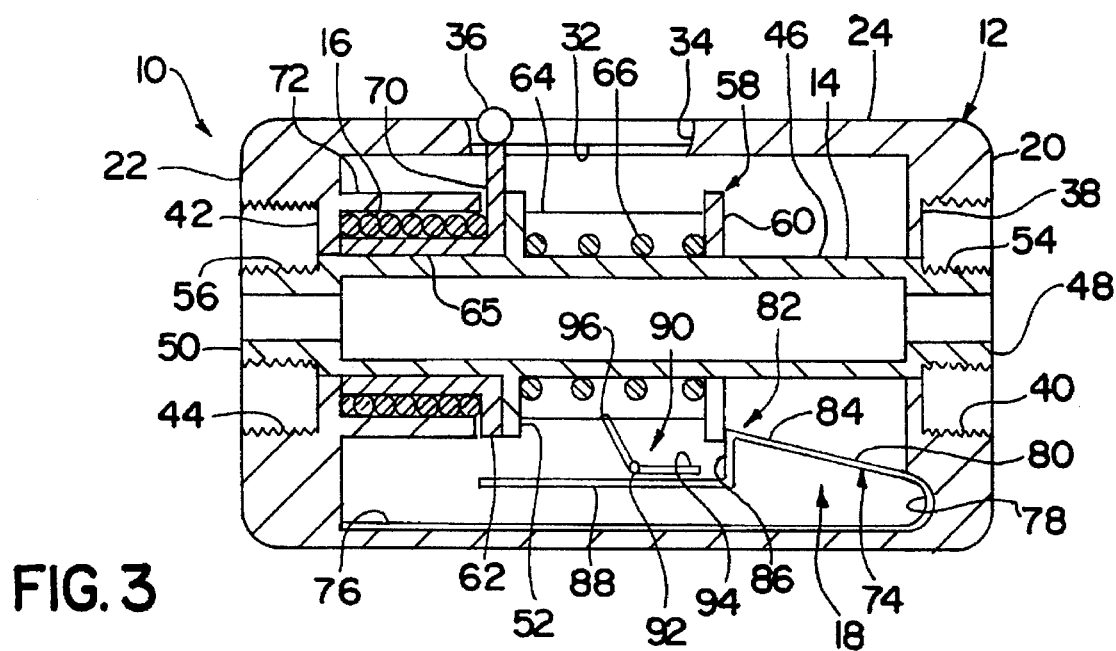
FIG. 3

MEDICAL INSTRUMENT WITH FORCE LIMITING MECHANISM

BACKGROUND OF THE INVENTION

1. Field of the Invention

The present invention relates to medical procedures and instruments and, more particularly, to a medical instrument that prevents probes from applying excessive force to anatomical tissue structures by retracting or protruding the probes.

2. Brief Description of the Related Art

In medical procedures, anatomical tissue structures are often contacted by medical personnel using medical probes specifically designed to push against or to pull the anatomical tissue structures. In many cases, however, there is a need to prevent the medical personnel from applying too much force to the anatomical tissue structures which can be damaged as a result of being pushed or pulled with excessive force. In the case of endoscopic procedures in particular, the problem is aggravated by the length of endoscopic instruments which can result in reduced "touching feel" for the surgeon.

SUMMARY OF THE INVENTION

Accordingly, it is a primary object of the present invention to overcome the above-mentioned disadvantages of the prior art and to provide a medical instrument that prevents medical probes from applying excessive force to anatomical tissue structures.

It is another object of the present invention to govern the force applied by medical probes to anatomical tissue structures by moving the medical probes in a direction opposite that of the applied force when a predetermined force threshold is exceeded.

Yet another object of the present invention is to protrude a medical probe relative to a handle of a medical instrument when a proximally directed pulling force exceeding a predetermined threshold is applied by the medical probe to an anatomical tissue structure.

Still another object of the present invention is to retract a medical probe relative to a handle of a medical instrument when a distally directed pushing force exceeding a predetermined threshold is applied by the medical probe to an anatomical tissue structure.

The present invention has another object in the use of opposite ends of a medical instrument for selectively protruding or retracting medical probes so as to reduce the force applied by the probes to anatomical tissue structures.

Some of the advantages of the medical instrument of the present invention are that the instrument permits medical personnel to use probes in a conventional manner or with automatic force reduction, that probes can be detachably mounted or formed integrally as part of the medical instrument, that the medical instrument facilitates disposal of detachable probes and reuse of mechanisms used for retracting or protruding the probes in order to reduce cost, and that development of a modular system of probes with standardized couplings is made possible. Also, by utilizing opposite ends of the medical instrument to selectively protrude or retract probes, the number of medical instruments required to be kept on hand for performing the above functions is reduced.

The present invention is generally characterized in a medical instrument including a housing, an elongate probe having a proximal end mounted by the housing and a distal end for applying a force to anatomical tissue, and force limiting means for moving the probe relative to the housing in a direction opposite the applied force when the applied force exceeds a predetermined threshold.

Another aspect of the present invention is generally characterized in a handle for medical probes including a housing having proximal and distal ends, mounting means disposed within the housing for mounting a probe, the mounting means being movable between an extended position proximate the distal end of the housing and a retracted position proximate the proximal end of the housing, retracting means for moving the mounting means proximally from the extended position to the retracted position, locking means for engaging the mounting means in the extended position to prevent the retracting means from moving the mounting means to the retracted position while permitting proximal movement of the mounting means in response to a proximal force acting on the mounting means, and releasing means for triggering release of the locking means when the proximal force exceeds a predetermined threshold to permit the retracting means to move the mounting means proximally from the extended position to the retracted position.

Yet another aspect of the present invention is generally characterized in a handle for medical probes including a housing having proximal and distal ends, mounting means disposed within the housing for mounting a probe, the mounting means being movable between an extended position proximate the distal end of the housing and a retracted position proximate the proximal end of the housing, extending means for moving the mounting means distally from the retracted position to the extended position, locking means for engaging the mounting means in the retracted position to prevent the extending means from moving the mounting means to the extended position while permitting distal movement of the mounting means in response to a distal force acting on a distal end of the mounting means, and releasing means for triggering release of the locking means when the distal force exceeds a predetermined threshold to permit the extending means to move the mounting means from the retracted position to the extended position.

A further aspect of the present invention is generally characterized in a handle for medical probes including a housing having first and second opposed ends, mounting means disposed within the housing and having first and second opposed ends, the first end of the mounting means having a configuration for mounting a first probe and the second end of the mounting means having a configuration for mounting a second probe, the mounting means being movable between a first position proximate the first end of the housing and a second position proximate the second end of the housing, bias means for biasing the mounting means toward the first end of the housing, locking means for locking the mounting means in the second position while permitting a predetermined amount of movement of the mounting means toward the first end of the housing, and releasing means responsive to movement of the mounting means beyond a predetermined position in the direction of the first end of the housing for triggering release of the locking means to permit the bias means to move the mounting means from the second position to the first position.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

FIG. 1 is a perspective view of a medical instrument according to the present invention.

FIG. 2 is an enlarged fragmentary side view of the medical instrument of FIG. 1.

FIG. 3 is a side view, partly in section, showing the handle of the medical instrument of FIG. 1.

DETAILED DESCRIPTION OF THE PREFERRED EMBODIMENTS

Figure 4:
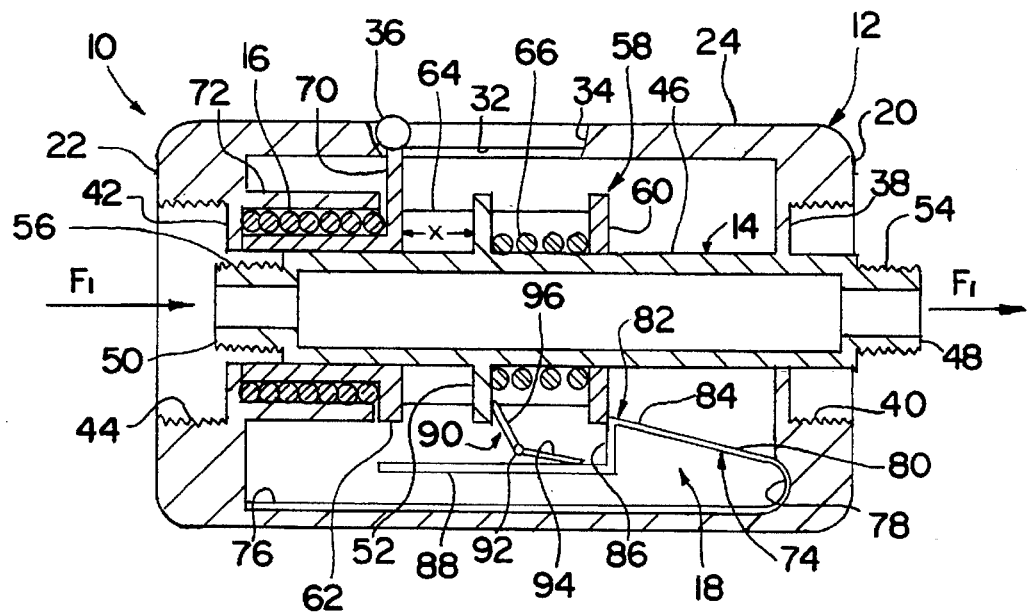
FIGS. 4 and 5 are side views, partly in section, illustrating operation of the medical instrument handle of FIG. 3.

The medical instrument of the present invention can be utilized to contact anatomical tissue using any type of probe; and, accordingly, while the medical instrument is described hereinafter as including a probe with a hook at a distal end, it is understood that the medical instrument can include other types of probes. By "probe," therefore, is meant any type of implement having a configuration useful for medical purposes including, for example, cutting members such as blades, penetrating members such as needles, cannulae such as portal sleeves, safety shields and catheters, cauteries, grasping implements such as hooks and forceps, biopsy tools and viewing probes such as endoscopes.

A medical instrument 10 according to the present invention, as illustrated in FIG. 1, includes a handle 11 and a medical probe 13 attached to the handle. Probe 13 includes a hollow cylindrical shaft 15 carrying a hook 17 at a distal end. Shaft 15 is fitted within a tubular sleeve 19 that is slidable over the shaft in a distal direction to cover hook 17 so that the instrument can be inserted through a portal in the wall of an anatomical cavity without snagging. As best seen in FIG. 2, distal end 21 of the shaft is closed; however, an aperture 23 can be formed at the distal end to communicate with the interior of the shaft as will be described in more detail below. Hook 17 extends distally from a lateral edge of the closed distal end 21 of the shaft and curves inwardly toward a diametrically opposed edge of the shaft. One or both of the proximal and distal edges 25 and 27 of the hook can be blunt or configured as cutting edges depending on the desirability of being used to manipulate or cut anatomical tissue.

Referring now to FIG. 3, handle 11 of the medical instrument is shown without any probes attached and without optional loop handles 26 and 28 for purposes of clarity. The handle 11 includes a housing 12, a tubular mounting member 14 slidably disposed within the housing, a bias member 16 for biasing the tubular mounting member toward a first position within the housing and a locking and releasing mechanism 18 for locking the tubular member in a second position within the housing and for releasing the tubular mounting member to be moved toward the first position in response to a predetermined axial force tending to move the tubular mounting member toward the first position.

Housing 12 can be made of any medically-acceptable material depending on the desirability of being sterilizable for reuse or disposable for single patient use and can have any desirable configuration in cross-section to facilitate grasping by a user or attachment of auxiliary handles such as the finger loops 26 and 28 shown in FIG. 1. The housing shown is generally cylindrical with axially opposed first and second end walls 20 and 22 disposed transverse or perpendicular to a longitudinal axis of the instrument and a cylindrical side wall 24 extending longitudinally between the first and second end walls. A longitudinal slot 32 is formed at the bottom of an elongate, trough-like recess 34 defined in the cylindrical side wall 24 to accommodate a knob 36, the function of which will be described in more detail below.

A first cylindrical recess 38 having internal threads 40 is formed in the first end wall 20 of the housing in coaxial alignment with the longitudinal axis of the handle and a second cylindrical recess 42 formed in the second end wall 22 of the housing. The second cylindrical recess 42 is similar in size and shape to the first cylindrical recess 38 and is internally threaded at 44. Recesses 38 and 42 are configured to couple with the proximal ends of medical probes or instruments to be held stationary relative to the housing and, as such, can have any configuration in cross-section and any size or shape for mating with the medical probes or instruments including, for example, the internally threaded cylindrical configurations shown or configurations utilizing conventional detents, Luer-locks and/or frictionally fitted parts.

Tubular member 14 includes a hollow cylindrical body 46 having axially opposed ends 48 and 50 of reduced diameter and an annular flange 52 disposed intermediate the axial ends of the cylindrical body. The first axial end 48 extends through an opening in the first end wall 20 of the housing to be disposed within recess 38 and is externally threaded at 54. The second axial end 50 extends through an opening in the second end wall 22 of the housing to be disposed within recess 42 and is externally threaded at 56. Axially opposed ends 48 and 50 are configured to couple with the proximal ends of medical probes to be moved and, as such, can have any configuration in cross-section and any size or shape for mating with the medical probes including, for example, the externally threaded cylindrical configurations shown or configurations utilizing conventional detents, Luer-locks and/or frictionally fitted parts.

Referring still to FIG. 3, a rail member 58 is disposed in housing 12 and is generally U-shaped including a first wall 60 disposed transverse or perpendicular to a longitudinal axis of the housing, a second wall 62 in configuration parallel to first wall 60 and a side wall 64 transversely joining the first and second walls of the rail member. A hollow cylindrical extension 65 extends from an opening in the second wall 62 of the rail member in the direction of the second end wall of the housing to serve as a guide for the tubular member and to function as a stop limiting movement of the rail member in the direction of the second end wall of the housing. Tubular member flange 52 is disposed between the first and second walls of the rail member with the rail member first wall 60 having an opening therein allowing passage therethrough by the cylindrical body 46 of the tubular member 14. The rail member first and second walls are disposed parallel or substantially parallel to flange 52, and a bias member 66 is connected between flange 52 and the rail member first wall 60 to bias the tubular member in the direction of the second end wall of the housing. As shown, bias member 66 includes a helical coil spring disposed around the cylindrical body of the tubular member and mounted in compression between flange 52 and the rail member first wall 60 to bias the tubular member in the direction of the second end wall causing flange 52 to abut the rail member second wall 62. However, bias member 66 can include various other types of springs as well as other types of bias devices including compression springs, tension springs, torsion springs, pan springs, leaf springs, rubber, plastic or magnets, for example. Rail member second wall 60 extends toward the cylindrical side wall 24 of housing 12, and a second, more powerful bias member 16 is mounted between the rail member second wall 62 and the second end wall 22 of housing 12 to bias the tubular member 14 in the direction of the first end wall 20 to an unloaded, rest position within the housing as will be explained further below. The bias member 16 can include a helical coil spring mounted in compression between the rail member second wall 62 and the second end wall 22 of the housing as shown, or the bias member can include any other type of spring or bias device as discussed above for bias member 66.

A post 70 extends upward from the rail member second wall 62 through slot 32 in the housing side wall 24 to terminate at knob 36 positioned in the elongate, trough-like recess 34 formed in the housing side wall. Slot 32 and recess 34 extend longitudinally in parallel with the longitudinal axis of the medical instrument 10. A cylindrical guide wall 72 extends from the second end wall 22 of the housing in the direction of the first end wall and is disposed around the second bias member 16. The cylindrical guide wall 72 terminates at a position aligned with a terminal end of the slot 32 to limit movement of the rail member in the direction of the second end wall and to laterally stabilize the rail member and tubular member as they are moved longitudinally within the housing.

Locking and releasing mechanism 18 for locking the tubular member 14 in a second, loaded position proximate the second end wall of the housing and for releasing the tubular member to allow the tubular member to move to the first, unloaded position proximate the first end wall of the housing includes a latch or locking spring 74, made of a strip of resilient material, formed to have a substantially longitudinal base 76 secured to the side wall 24 of housing 12 and a bend 78 joining the base 76 with an upwardly angled arm 80 spaced from the base. Arm 80 carries or forms a latch 82 having an angled latching surface 84 joining a vertical latching surface 86 disposed substantially transverse to the longitudinal axis of the medical instrument and substantially parallel to the rail member first wall 60. Arm 80 has an extension 88 extending from the bottom of latch 82 toward the second end wall 22, and a releasing member or trigger 90 is juxtaposed with extension 88. The trigger 90 is pivotally mounted in housing 12 on a pin 92 secured to a wall or walls of the housing or structure supported in the housing, and the trigger is generally L-shaped with a leg 94 overlying extension 88 and a leg 96 extending transversely from leg 94 but at a slight angle toward the second end wall 22 of the medical instrument. A torsion spring (not shown) is coiled around pin 92 and fixed to trigger 90 to bias the trigger clockwise, looking at FIG. 3, such that leg 94 is biased toward arm extension 88.

Figure 5:
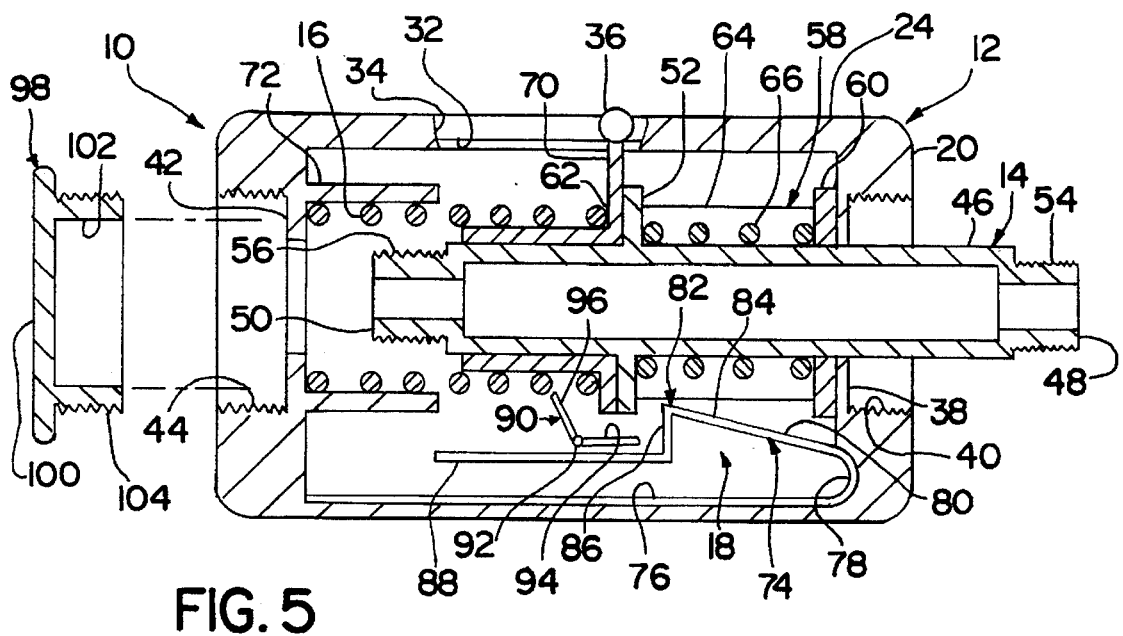

In use, the handle 11 is preferably supplied in the unloaded rest condition shown in FIG. 5 with or without medical probes attached. In the unloaded condition, bias member 16 holds rail member 58 proximate the first end wall 20 of the housing so that the first wall 60 of the rail member abuts the first end wall and knob 36 is disposed at the end of slot 32 nearest the first end wall of the housing. Also, tubular member 14 is biased by spring 66 toward a rest position where tubular member flange 52 abuts the second wall 62 of the rail member 58 and first and second ends 48 and 50 of the tubular member are disposed externally of and within the housing 12, respectively.

Medical probes can be mounted on either side of the handle 11 by coupling proximal ends of the probes with one of the first and second ends 48 and 50 of the tubular member 14. If the handle 11 is maintained in the unloaded condition shown in FIG. 5 the medical probes can be used in a conventional manner without being protruded or retracted relative to the housing when a predetermined axial force is exceeded. If, on the other hand, the user desires the medical probes to be automatically moved in a direction opposite the force being applied by the probes when the applied force exceeds a predetermined threshold, for example to prevent excessive force from being applied to anatomical tissue structures, the medical probe can be mounted on the first end 48 of the tubular member for being protruded (i.e., moved away from the housing) when pulled excessively or on the second end 50 for being retracted (i.e., moved toward the housing) when pushed too hard.

A medical probe, such as probe 13 shown in FIGS. 1 and 2, can be mounted on the first end 48 of the tubular member by threading a proximal end of the medical probe onto the first end of the tubular member when the handle 11 is in the unloaded condition shown in FIG. 5. Alternatively, the probe can be mounted on the second end 50 of the tubular member by threading the proximal end of the probe on the second end of the tubular member.

Regardless of which end carries a medical probe, the medical instrument 10 can be loaded or cocked by drawing the knob 36 along slot 32 in the direction of the second end wall 22 of the housing to move the rail member 58, and thus the tubular member 14, towards the second end wall of the housing. As the knob 36 is drawn toward the second end wall, the first wall 60 of the rail member 58 slides over the angled latch surface 84 moving the latch 82 away from the longitudinal axis of the medical instrument and allowing the first wall of the rail member to move past the latch. Latch spring 74 springs back toward the longitudinal axis of the medical instrument as the rail member is moved toward the second end wall and, as a result, the transverse latching surface 86 is then disposed between the rail member first wall 60 and the first end wall 20 of the housing to prevent movement of the rail member toward the first end wall. Bias member 16 is compressed between the rail member second wall 62 and the second end wall 22 of the housing and is held in compression when the rail member is locked by spring 74. Tubular member flange 52 can move between the walls of the rail member 58 when the rail member is locked against latch 82 but is biased toward the rest position proximate the second wall 62 of the rail member by bias member 66. With the rail member locked and the tubular member in the rest position shown in FIG. 3, tubular member flange 52 is disposed between the transverse leg 96 of trigger 90 and the second end wall 22 of the housing 12.

When, during use of a medical probe, a force $F_1$ is exerted on the tubular member 14 which tends to cause the tubular member to move away from the rest position shown in FIG. 3 a predetermined distance x as shown in FIG. 4, tubular member flange 52 will engage trigger leg 96 causing the trigger 90 to rotate clockwise looking at FIG. 4. Clockwise rotation of trigger 90 causes leg 94 overlying arm extension 88 to press down on the extension moving the latch 82 away from the longitudinal axis of the medical instrument 10. Latching surface 86 is thus disengaged from the rail member wall 60 permitting the bias member 16 to move the rail member 58, and thus the tubular member 14, in the direction of the force and toward the first end wall 20 of the medical instrument as shown in FIG. 5.

If, for example, the medical probe is a hooking implement mounted on the first end 48 of the tubular member and the force $F_1$ is caused by resistance of a vessel or other anatomical tissue structure to being pulled by the probe, it will be appreciated that movement of the tubular member 14 in the direction of the force will counteract further pulling of the vessel by the probe thereby limiting or reducing the force applied by the probe. If, on the other hand, the medical probe is mounted on the second end 50 of the tubular member and the force $F_1$ is caused by resistance of anatomical tissue to being pushed by the probe, it will be appreciated that movement of the tubular member 14 in the direction of the force will counteract further pushing of the anatomical tissue by the probe thereby limiting or reducing the force applied by the probe.

It will also be appreciated that since the force $F_1$ necessary to move the tubular member 14 a predetermined distance x is related to the spring constant of bias member 66, smaller or larger threshold forces can be chosen by altering the distance x to be traveled by the tubular member flange or by choosing a bias member with an appropriate spring constant.

Referring still to FIG. 5, a cap 98 is shown for closing an endwall of the housing. The cap 98 includes a round flange 100 and a cylindrical body 102 extending from one side of the flange and having external threads 104 for mating with the internal threads in recesses 38 and 42. Similar caps can be used to close the first and second end walls 20 and 22 of the housing when the medical instrument is in the loaded condition shown in FIG. 3, or one cap can have a longer cylindrical body than the other cap to close the first end wall and to cover the first end of the tubular member when the medical instrument is in the unloaded condition shown in FIG. 5. Both ends can be capped when the medical instrument 10 is not in use and/or a single cap can be used when it is desired to close only one end of the medical instrument so that the other, uncapped end can be used.

Recesses 38 and 42 can also be used to mount additional medical probes, such as sleeves, so that, for example, when a first medical probe is mounted on the first end of the tubular member, a sleeve mounted in recess 38 can be positioned over the distal end of the first medical probe to ease insertion of the probe through a portal housing and to prevent snagging of anatomical tissue. Once inserted into an anatomical cavity, the sleeve can be repositioned to expose the distal end of the medical probe so that the medical probe can be used to contact anatomical tissue. Also, when a medical probe is mounted on the second end of the tubular member, a sleeve can be mounted in recess 42 in a fixed position exposing the distal end of the probe when the rail member is locked and protecting the distal end of the probe when the tubular member is moved to the position shown in FIG. 5.

Figure 6:
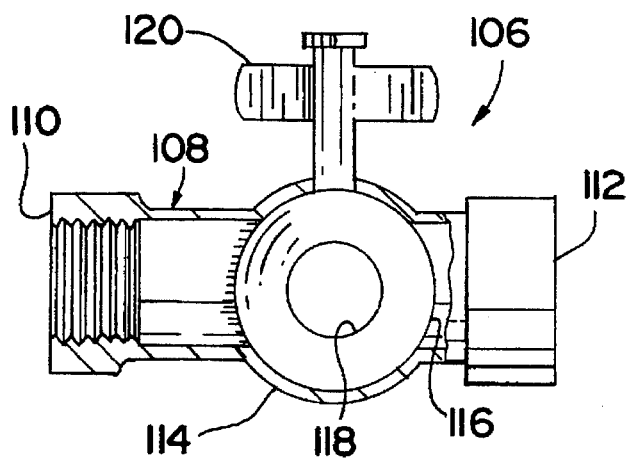
FIG. 6 is a side view, partly in section, of a detachable valve for use with the medical instrument of the present invention.

FIG. 6 illustrates a detachable stopcock valve 106 that can be mated with one of the ends of tubular member 14 to regulate the flow of fluids through the tubular member and any hollow probes, like probe 13, that are mounted on the opposite end of the tubular member. Valve 106 includes a cylindrical pipe section 108 having a threaded distal end 110 configured to mate with the tubular member 14, a proximal end 112 configured to provide a point of entry for inserting medical instruments and to couple with conventional fluid sources or pumps, and a hollow spherical portion 114 disposed intermediate the proximal and distal ends of the pipe section. A spherical valve member 114 with a cylindrical bore 116 is disposed within the spherical portion 114 and is connected with a T-shaped handle 118 disposed externally of the spherical portion for selectively rotating the valve member between an open position where the bore 116 is aligned with a longitudinal axis of the pipe section and a closed position where the bore faces an interior surface of the spherical portion of the pipe section.

Figure 7:
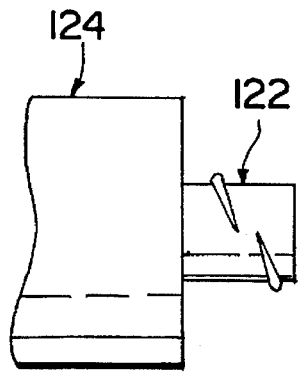
FIGS. 7–9 are side views of modified couplings for the medical instrument of the present invention.
Figure 8:
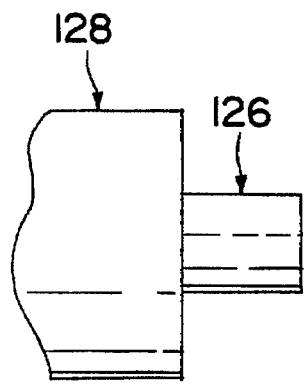
Figure 9:
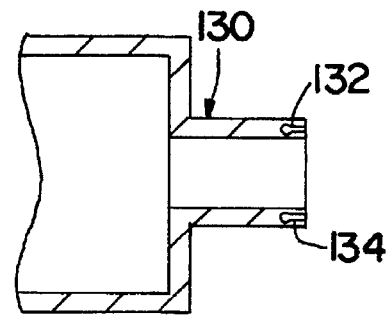

FIGS. 7–9 each illustrate one end of a modified tubular member. It will be appreciated, however, that axially opposed ends of a tubular member can have similar or different configurations for mounting medical probes or auxiliary devices, like stopcock 106, and that the end configurations shown can be utilized in any combination desired. FIG. 7 illustrates a modified end configuration 122 for a tubular member 124 wherein the tubular member is similar to tubular member 14 and the end 122 resembles a conventional Luer-lock connector. Another modified end configuration for a tubular member is shown in FIG. 8 at 126 wherein the tubular member 128 is similar to tubular member 14 and the end 126 is configured to frictionally fit within a recess formed in the proximal end of a medical probe or an auxiliary device. The modified end configuration 130 shown in FIG. 9 is similar to those described above but includes a pair of detents 132 and 134 for being coupled with mating detent structure on the proximal end of a medical probe or an auxiliary device.

In the embodiments shown, the cylindrical body of the tubular member fits through openings in the end walls of the housing and the tubular member end configurations include projecting portions of smaller diameter than the cylindrical body to facilitate passage of the ends through the openings in the end walls when probes are attached to the tubular member. The end configurations could, however, be the same size as, or larger than, the cylindrical body of the tubular member if the openings are enlarged or if it is desired that the ends not be movable through the openings in the end walls. Furthermore, the tubular body can be configured so that, in the unloaded condition, the ends of the tubular body do not extend beyond the end walls of the housing.

From the above, it will be appreciated that use of the medical instrument of the present invention to contact anatomical tissue with medical probes prevents the probes from applying excessive force to the anatomical tissue by moving the probes in a direction opposite that of the applied force when a predetermined force threshold is exceeded. By "probes" is meant any type of implement having a configuration useful for medical purposes including, for example, cutting members such as blades, penetrating members such as needles, cannulae such as portal sleeves, safety shields and catheters, cauteries, grasping implements such as hooks and forceps, biopsy tools and viewing probes such as endoscopes. The probes can be integrally formed as part of the medical instrument or can be detachably mounted to be removable; and when the probes are removable, the medical instrument of the present invention permits development of a modular system whereby, for example, medical personnel can match medical probes with an appropriate handle having a desired characteristic, such as a threshold force for triggering retraction or extension of the probes, to suit the particular procedure being performed. Use of the medical instrument can also reduce waste by facilitating disposal of exhausted medical probes and reuse of the medical instrument with new medical probes, thereby reducing cost and simplifying sterilization procedures as well.

The medical instrument can be configured to perform one or both of the functions of retracting or protruding a probe when a predetermined threshold force is exceeded; however, by combining retracting and extending mechanisms in one medical instrument the number of parts required for performing retracting and extending functions can be reduced and the efficiency of medical personnel can be increased by reducing the number of medical instruments from which medical personnel must choose in order to obtain one or both of a retracting and extending function.

The medical instrument of the present invention can be used in any type of medical procedure, whether therapeutic or diagnostic, including open or endoscopic procedures. The components of the medical instrument can be made of any suitable, medical grade material to permit sterilization for reuse or for single patient use. The components can be made of multiple parts of various configurations and materials to reduce cost. Furthermore, various valves, stopcocks and seals can be mounted within the housing to control fluid flow through the various components of the instrument, and conventional electrical connectors can be mounted on the medical instrument and coupled with the probes to perform electrosurgical procedures such as cautery and cutting.

When the medical instrument is configured with detachable probes, the mating portions of the probes and/or any auxiliary devices, such as valve 106, can have any configuration for being coupled with the handle of the medical instrument, including threaded or smooth projecting portions or nubs, threaded or smooth recesses, conventional detent structures, sockets or collars, opposed jaws, Luer locks or any other type of coupling mechanism, including those disclosed in Applicant's pending U.S. patent application Ser. No. 08/362,223, filed Dec. 23, 1994, pending, the disclosure of which is incorporated herein by reference.

Auxiliary handles, such as loop handles 26 and 28, can be mounted by the housing and coupled with conventional force transmitting elements to operate probes having articulable components, such as grasping or needle holding forceps. The auxiliary handles can have any configuration to be grasped by the user including, for example, resilient U-shaped handles, pistol grips and scissor-type handles.

The rail member can have various configurations to engage the latch and be released by the trigger. Preferably, the rail member will have a configuration to serve as a stop or abutment for the tubular member as exemplified herein by the U-shaped portion of the rail member. When a knob is provided for manually moving the tubular member within the housing, the knob can be coupled with the tubular member directly or via the rail member mounting the tubular member. Indicator strips can also be attached to the knob in a manner to be visible through the slot in the housing through which the knob protrudes. The indicator strip can be color coded and/or provided with other markings to indicate the position of the tubular member to which the knob is attached.

Release of the locking mechanism can be triggered by movement of an operating member, such as flange 52, carried on any component of the medical instrument movable in response to a resistant force from tissue contact. The operating member is, however, preferably carried by the tubular member so as to limit the number of components in the medical instrument. Alternatively, operating members could be carried on additional members such as, for example, a slender rod disposed within or alongside one of the probes.

The locking and releasing mechanisms require only a latch for locking the rail member in the loaded position and a trigger for releasing the latch in response to an axial force exceeding a predetermined threshold; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing in various ways to minimize the length of the housing and, therefore, the overall length of the medical instrument.

Various locking and releasing mechanisms that can be simply modified for use in the medical instrument of the present invention are disclosed in Applicant's pending applications Ser. No. 07/800,507, filed Nov. 27, 1991, abandoned, Ser. No. 07/805,506, filed Dec. 6, 1991, now U.S. Pat. No. 5,330,432, Ser. No. 07/808,325, filed Dec. 16, 1991, now U.S. Pat. No. 5,324,268, Ser. No. 07/848,838, filed Mar. 10, 1992, now U.S. Pat. No. 5,445,617, Ser. No. 07/868,566, now U.S. Pat. No. 5,320,600 and Ser. No. 07/868,578, now U.S. Pat. No. 5,336,176 filed Apr. 15, 1992, Ser. No. 07/929,338, filed Aug. 14, 1992, now U.S. Pat. No. 5,360,405, Ser. No. 07/845,177, filed Sep. 15, 1992, abandoned, Ser. No. 07/945,177, filed Sep. 15, 1992, pending, Ser. No. 08/079,586, filed Jun. 22, 1993, now U.S. Pat. No. 5,423,770 Ser. No. 08/195,512, filed Feb. 14, 1994, pending, Ser. No. 08/196,029, filed Feb. 14, 1994, pending, Ser. No. 08/196,027, filed Feb. 14, 1994, pending, Ser. No. 08/195,178, filed Feb. 14, 1994, now U.S. Pat. No. 5,536,256, Ser. No. 08/237,734, filed May 4, 1994, pending, Ser. No. 08/247,205, filed May 20, 1994, pending, Ser. No. 08/254,007, filed Jun. 3, 1994, now U.S. Pat. No. 5,478,317, and Ser. No. 08/260,439, filed Jun. 15, 1994, now U.S. Pat. No. 5,423,760 the disclosures of which are incorporated herein by reference. The above applications disclose automatically retracting safety penetrating instruments such that modification of the locking and releasing mechanisms requires reversing the trigger members to release the latches in response to a predetermined amount of movement of an operating member against a bias member. The above applications also disclose various bias arrangements useful with the medical instrument of the present invention. Other locking and releasing mechanisms that can be simply modified for use in the medical instrument of the present invention are disclosed in Applicant's pending applications Ser. No. 08/279,170, pending, and 08/279,172 filed Jul. 22, 1994, pending.

One or more control buttons such as the control buttons described in Applicant's copending patent application Ser. No. 08/083,220, filed Jun. 24, 1993, now U.S. Pat. No. 5,431,635, can be mounted next to any latch for manually disengaging the latch to prevent locking of the medical instrument in the loaded position. In addition, any latch arm or separate spring can carry a secondary pawl or latch at one end for locking the rail member in the unloaded position shown in FIG. 5 such that the medical probes can be used in a conventional manner without the force limiting feature of the present invention. The latches can then be released by use of a control button as described above so that the medical instrument can be cocked or loaded.

The various features of the disclosed embodiments can be combined dependent upon operational requirements and the complexity of the medical instrument.

Inasmuch as the present invention is subject to many variations, modifications and changes in detail, it is intended that all subject matter discussed or shown in the accompanying drawings be interpreted as illustrative only and not be taken in a limiting sense.

What is claimed is:

1. A medical instrument comprising
   a housing;
   an elongate probe having a proximal end mounted to said housing and a distal end for applying a force to anatomical tissue; and
   force limiting means for moving said probe relative to said housing in a direction opposite said applied force in response to said applied force exceeding a predetermined threshold.

2. A medical instrument as recited in claim 1 wherein said force applied to anatomical tissue by said distal end of said probe is a distal force and said force limiting means moves said probe proximally relative to said housing.

3. A medical instrument as recited in claim 2 wherein said housing has proximal and distal ends and said force limiting means includes bias means for biasing said probe proximally, locking means for locking said probe proximate said distal end of said housing and releasing means for releasing said locking means to permit said bias means to move said probe proximally when said applied force exceeds a predetermined threshold.

4. A medical instrument as recited in claim 3 wherein said locking means permits proximal movement of said probe and said releasing means triggers release of said locking means when said probe moves proximally a predetermined distance.

5. A medical instrument as recited in claim 1 wherein said force applied to anatomical tissue by said distal end of said probe is a proximal force and said force limiting means moves said probe distally relative to said housing.

6. A medical instrument as recited in claim 5 wherein said housing has proximal and distal ends and said force limiting means includes bias means for biasing said probe distally, locking means for locking said proximal end of said probe proximate said proximal end of said housing and releasing means for releasing said locking means to permit said bias means to move said probe distally when said applied force exceeds a predetermined threshold.

7. A medical instrument as recited in claim 6 wherein said locking means permits distal movement of said probe and said releasing means triggers release of said locking means when said probe moves distally a predetermined distance.

8. A handle for medical probes comprising a housing having proximal and distal ends;

mounting means disposed within said housing for mounting a probe, said mounting means being movable between an extended position proximate said distal end of said housing and a retracted position proximate said proximal end of said housing;

retracting means for moving said mounting means proximally from said extended position to said retracted position;

locking means for engaging said mounting means in said extended position to prevent said retracting means from moving said mounting means to said retracted position while permitting proximal movement of said mounting means in response to a proximal force acting on said mounting means; and releasing means for triggering release of said locking means when said proximal force exceeds a predetermined threshold to permit said retracting means to move said mounting means proximally from said extended position to said retracted position.

9. A handle as recited in claim 8 wherein said mounting means includes a distal end configured to mate with a proximal end of the probe.

10. A handle as recited in claim 9 wherein said distal end of said mounting means includes a nub configured to be frictionally received within a recess formed in the proximal end of the probe.

11. A handle as recited in claim 9 wherein said distal end of said mounting means is threaded for engaging threads formed at the proximal end of the probe.

12. A handle as recited in claim 9 wherein said distal end of said mounting means includes detents for engaging mating detent structure at the proximal end of the probe.

13. A handle as recited in claim 8 and further comprising a rail member disposed within said housing and having first and second walls, said rail member being movable within said housing between an extended position proximate said distal end of said housing and a retracted position proximate said proximal end of said housing, wherein said mounting means includes a cylindrical body extending distally through an opening in said first wall of said rail member and a flange disposed on said cylindrical body between said first and second walls of said rail member and wherein said locking means engages said rail member to lock said mounting means.

14. A handle as recited in claim 13 and further comprising bias means for biasing said flange distally toward said first wall of said rail member.

15. A handle as recited in claim 8 and further comprising a knob coupled with said mounting means for manually moving said mounting means distally from said retracted position to said extended position.

16. A handle for medical probes comprising a housing having proximal and distal ends;

mounting means disposed within said housing for mounting a probe, said mounting means being movable between an extended position proximate said distal end of said housing and a retracted position proximate said proximal end of said housing;

extending means for moving said mounting means distally from said retracted position to said extended position;

locking means for engaging said mounting means in said retracted position to prevent said extending means from moving said mounting means to said extended position while permitting distal movement of said mounting means in response to a distal force acting on a distal end of said mounting means; and releasing means for triggering release of said locking means when said distal force exceeds a predetermined threshold to permit said extending means to move said mounting means from said retracted position to said extended position.

17. A handle as recited in claim 16 wherein said mounting means includes a distal end configured to mate with a proximal end of the probe.

18. A handle as recited in claim 17 wherein said distal end of said mounting means includes a nub configured to be frictionally received within a recess formed in the proximal end of the probe.

19. A handle as recited in claim 17 wherein said distal end of said mounting means is threaded for engaging threads formed at the proximal end of the probe.

20. A handle as recited in claim 17 wherein said distal end of said mounting means includes detents for engaging mating detent structure at the proximal end of the probe.

21. A handle as recited in claim 16 and further comprising a rail member disposed within said housing and having first and second walls, said rail member being movable within said housing between an extended position proximate said distal end of said housing and a retracted position proximate said proximal end of said housing, wherein said mounting means includes a cylindrical body extending distally through an opening in said first wall of said rail member and a flange disposed at a proximal end of said cylindrical body between said first and second walls of said rail member and wherein said locking means engages said rail member to lock said mounting means.

22. A handle as recited in claim 21 and further comprising bias means for biasing said flange proximally toward said second wall of said rail member.

23. A handle as recited in claim 16 and further comprising a knob coupled with said mounting means for manually moving said mounting means proximally from said extended position to said retracted position.

24. A handle for medical probes comprising a housing having first and second opposed ends;

mounting means disposed within said housing and having first and second opposed ends, said first end of said mounting means having a configuration for mounting a first probe and said second end of said mounting means having a configuration for mounting a second probe, said mounting means being movable between a first position proximate said first end of said housing and a second position proximate said second end of said housing;

bias means for biasing said mounting means toward said first end of said housing;

locking means for locking said mounting means in said second position while permitting a predetermined amount of movement of said mounting means toward said first end of said housing; and releasing means responsive to movement of said mounting means beyond a predetermined position in the direction of said first end of said housing for triggering release of said locking means to permit said bias means to move said mounting means from said second position to said first position.

25. A handle as recited in claim 24 wherein said first end of said mounting means is configured to mate with a proximal end of the first probe.

26. A handle as recited in claim 25 wherein said first end of said mounting means includes a nub configured to be frictionally received within a recess formed in the proximal end of the first probe.

27. A handle as recited in claim 25 wherein said first end of said mounting means is threaded for engaging threads formed at the proximal end of the first probe.

28. A handle as recited in claim 25 wherein said first end of said mounting means includes detents for engaging mating detent structure at the proximal end of the first probe.

29. A handle as recited in claim 24 wherein said second end of said mounting means is configured to mate with a proximal end of the second probe.

30. A handle as recited in claim 29 wherein said second end of said mounting means includes a nub configured to be frictionally received within a recess formed in the proximal end of the second probe.

31. A handle as recited in claim 29 wherein said second end of said mounting means is threaded for engaging threads formed at the proximal end of the second probe.

32. A handle as recited in claim 29 wherein said second end of said mounting means includes detents for engaging mating detent structure at the proximal end of the second probe.

33. A handle as recited in claim 24 and further comprising a rail member disposed within said housing and having first and second walls, said rail member being movable within said housing between an extended position proximate said first end of said housing and a retracted position proximate said second end of said housing, wherein said mounting means includes a cylindrical body extending through openings in said first and second walls of said rail member and a flange carried by said cylindrical body between said first and second walls of said rail member and wherein said locking means engages said rail member to lock said mounting means.

34. A handle as recited in claim 33 and further comprising bias means for biasing said flange toward said second end of said housing into abutment with said second wall of said rail member.

35. A handle as recited in claim 24 and further comprising a knob coupled with said mounting means for manually moving said mounting means from said first position to said second position.

* * * * *